United States Patent [19]
Bahr

[11] Patent Number: 6,099,470
[45] Date of Patent: Aug. 8, 2000

[54] MONITOR FOR DIFFUSABLE CHEMICAL SUBSTANCE

[75] Inventor: Pontus Von Bahr, Stockholm, Sweden

[73] Assignee: Siemens Elema AB, Solna, Sweden

[21] Appl. No.: 09/236,516

[22] Filed: Jan. 25, 1999

[30] Foreign Application Priority Data

Mar. 5, 1998 [SE] Sweden ................................. 9800693

[51] Int. Cl.⁷ .............................. A61M 1/34; G01N 33/48
[52] U.S. Cl. .......................... 600/366; 600/309; 422/68.1
[58] Field of Search .................................... 600/309, 348, 600/352, 364, 365, 366; 604/19, 48, 93, 318; 422/68.1; 204/403, 415

[56] References Cited

U.S. PATENT DOCUMENTS

| | | |
|---|---|---|
| 4,221,567 | 9/1980 | Clark et al. . |
| 4,274,417 | 6/1981 | Delpy ..................................... 600/364 |
| 5,058,416 | 10/1991 | Engelhardt et al. . |
| 5,148,811 | 9/1992 | Messinger . |
| 5,248,616 | 9/1993 | Beckman et al. ...................... 422/68.1 |

FOREIGN PATENT DOCUMENTS 0 549 394  6/1993  France .

*Primary Examiner*—Eric F. Winakur
*Attorney, Agent, or Firm*—Hill & Simpson

[57] ABSTRACT

A monitor for analyzing a body fluid for diffusable chemical substances has a liquid filled probe, for example a catheter, having a region contactable with the body fluid within the body and permeable to chemical substances of interest. A sensor unit is in liquid communication with the probe and has sensors, each with an output dependent on the presence of a chemical substance of interest. A periodic analysis of the probe liquid is provided from the sensor unit and a pumping system is adapted to circulate the probe liquid around a closed liquid flow path, including the permeable region of the probe, a number of times in each period between the analysis of the liquid.

6 Claims, 3 Drawing Sheets

6,099,470

MONITOR FOR DIFFUSABLE CHEMICAL SUBSTANCE

BACKGROUND OF THE INVENTION

1. Field of the Invention

The present invention relates to a monitor for diffusable chemical substances and in particular to a monitor which may be used to analyze an animal (including human) body fluid to determine the presence of diffusable chemical substances.

2. Description of the Prior Art

In order to provide an optimal treatment for a patient, for instance during intensive care, it is important to collect information on the condition of that patient on a regular basis. Important information can be obtained by analyzing the blood of the patient to determine the presence and amount of diffusable chemical substances such as blood gasses, electrolytes, metabolites (such as glucose or urea) or $H^+$ ions.

It is also important that a monitor used for this type of regular analysis take away as little of the body fluid (such as blood) from the patient as possible. Otherwise the cumulative effect of many individual determinations could itself be detrimental to the patient.

A monitor for the in vivo determination of the presence of diffusable chemicals within a body fluid in which none of the fluid is withdrawn from the patient is described in U.S. Pat. No. 4,221,567. The monitor has a liquid filled probe with a permeable membrane which, when inserted into the body fluid, allows the chemical substances of interest to pass between the body fluid and the liquid. Sensors sensitive sensitive to the chemical substance of interest are placed along the flow path of the liquid; in the probe. A pump transports liquid from the region of the membrane for analysis by the sensors after equilibrium is reached among the diffusable chemicals in the body fluid and in the liquid.

Since the sample volume of liquid that contains the diffused chemicals is relatively small compared to the volume of liquid between the sensors and the membrane in this known monitor, the pump must operate accurately in order to ensure that liquid from the correct region of the probe is analyzed by the sensors. Moreover, the pump must transport the liquid in a smooth yet quick manner in order to avoid dispersion of the chemical substances from the equilibrated volume. All of this requires a relatively expensive pumping and control system.

SUMMARY OF THE INVENTION

It is an object of the present invention to provide a body fluid monitor which allows for a larger sampling volume and which alleviates the pumping problems associated with the previously described device.

The above object is achieved in accordance with the invention in a monitor for analyzing a body fluid for diffusable chemical substances having a liquid-filled probe with a region that can be brought into communication or contact with the body fluid within a patience's body, this region being permeable to the chemical substances of interests, a sensor unit in fluid communication with the probe having at least one sensor which emits a signal dependent on the presence of a particular chemical substance of interest, and a pumping system for transporting a sample of liquid in the probe from the permeable region to the sensor unit for analysis therein, the sensor unit and the pumping system cooperating to provide an analysis of the probe liquid after it has been circulated a number of times around a closed fluid flow path.

By arranging for the liquid to be reticulated relatively quickly a larger sampling volume, and preferably the entire liquid volume of the closed flow path, is provided for periodic analysis, thus allowing a less accurate pumping and control system to be used. Moreover the dispersion that inevitably occurs serves to accelerate the diffusion of chemicals across the permeable membrane of the probe.

Preferably the pumping system includes a pump, such as a relatively inexpensive peristaltic pump, adapted to provide a pulsating liquid flow. This may further accelerate the dispersion of the diffusable chemicals throughout the probe liquid to further enhance their diffusion rates across the permeable barrier. While any sensors of the sensor unit may be positioned along the flow path of the probe, it may be advantageous to separate the sensor unit from the probe and to provide an extraction instrument, such as a microliter syringe pump, a reduced pressure ampule or simply a valve arrangement, positioned to extract a sample from the probe and deliver it to sensors within the sensor unit. In this way, the flow through the sensors is made independent of the flow through the probe, so that the response times of the sensors need not be matched to the circulation rate of the liquid. This allows the system to have a fast continuous flow within the probe while reducing the demands on the sensors. Moreover the separation of sensor unit and liquid flow path may reduce systematic noise, such as may be caused by mechanical movement of the sensor unit as a result of the pulsating or rapid flow, and so increase the sensitivity of the monitor.

DESCRIPTION OF THE DRAWINGS

FIG. $1^a$ shows a patient connected to intensive care equipment, including a monitor according to the present invention FIG. $1^b$ shows the connection, via a catheter, of the inventive monitor to the circulatory system of a patient.

DESCRIPTION OF THE PREFERRED EMBODIMENTS

Figure 1A:
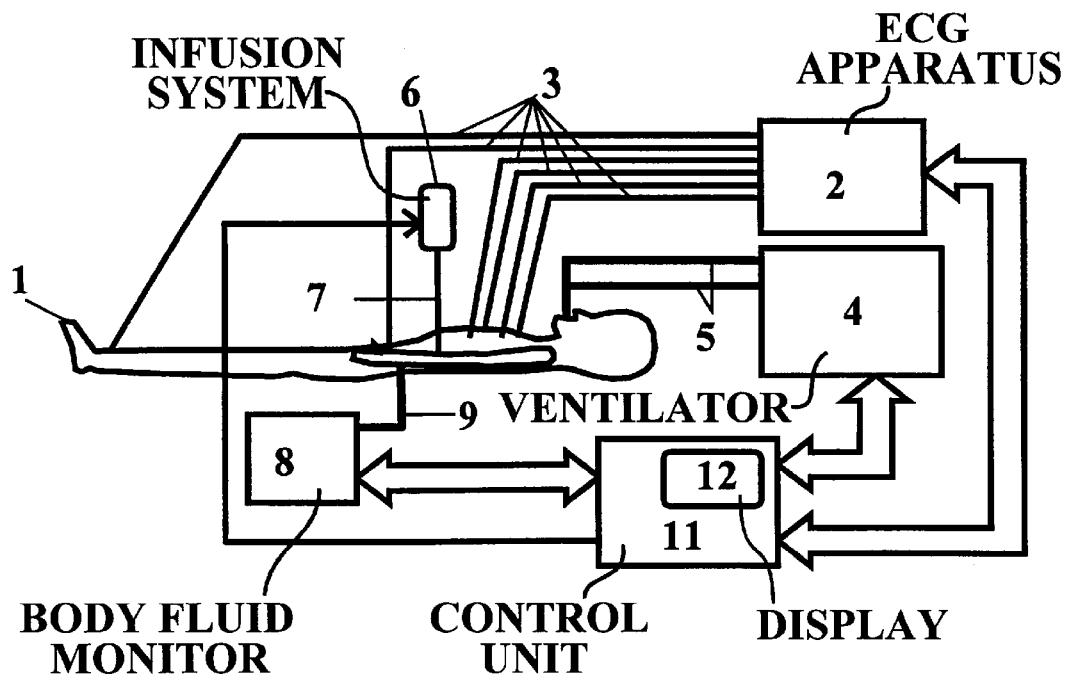

As shown in FIGS. $1^a$ and $1^b$ a patient 1 is connected to a number of items of intensive care equipment typically employed in an intensive care unit of a hospital. The patient 1 is for instance connected to an ECG apparatus 2 which, via electrodes 3 connected at different positions on the patient 1, records and analyzes the patient's heart signals. Further a ventilator 4 is connected to the patient 1 via gas lines 5 for supporting or controlling the patient's respiration. An infusion system 6 is connected to the patient 1 via an infusion line 7 for providing the patient with nutrient solution, plasma or other substances which can be infused during intensive care. A monitor 8 according to the invention includes a catheter 9 for communication with the system of the patient 1 and a housing 10 in which is placed a sensor unit (not shown). For clarity, the catheter 9 is shown with a disproportional length. In reality, the catheter 9 should be as short as possible to reduce the total liquid volume in the catheter and to accelerate that volume reaching equilibrium with the blood. The arrangement 8 will therefore normally be located very close to, if not in direct contact with, the patient 1 as illustrated in FIG. 1b.

A central control unit 11 is connected to all apparatus units 2, 4, 6, 8 involved in the intensive care treatment of the patient 1 for recording, analyzing and controlling (automatically or by prompting changes) the treatment given to the patient 1. A display 12 can display different curves or measurement results relating to the patient 1, such as ECGs, respiration curves, blood gas content, etc.

Figure 1B:
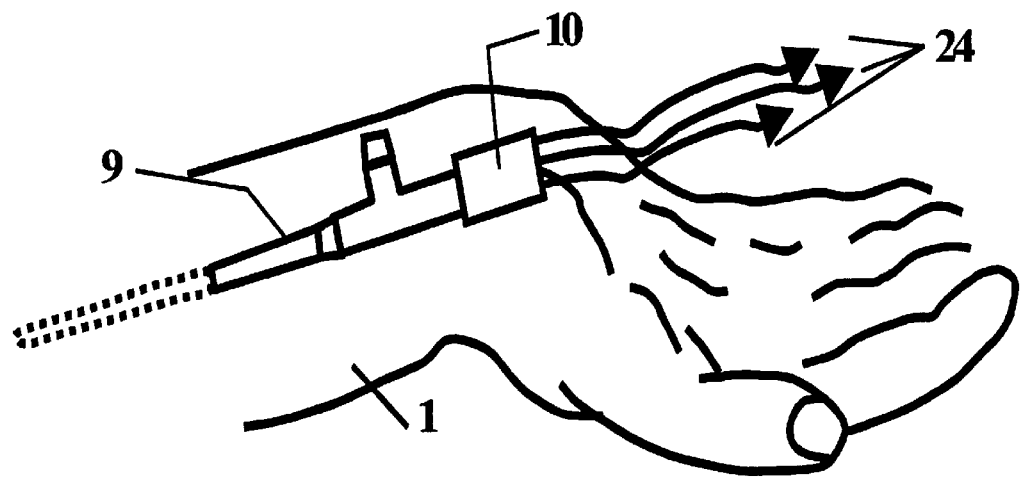
Figure 2:
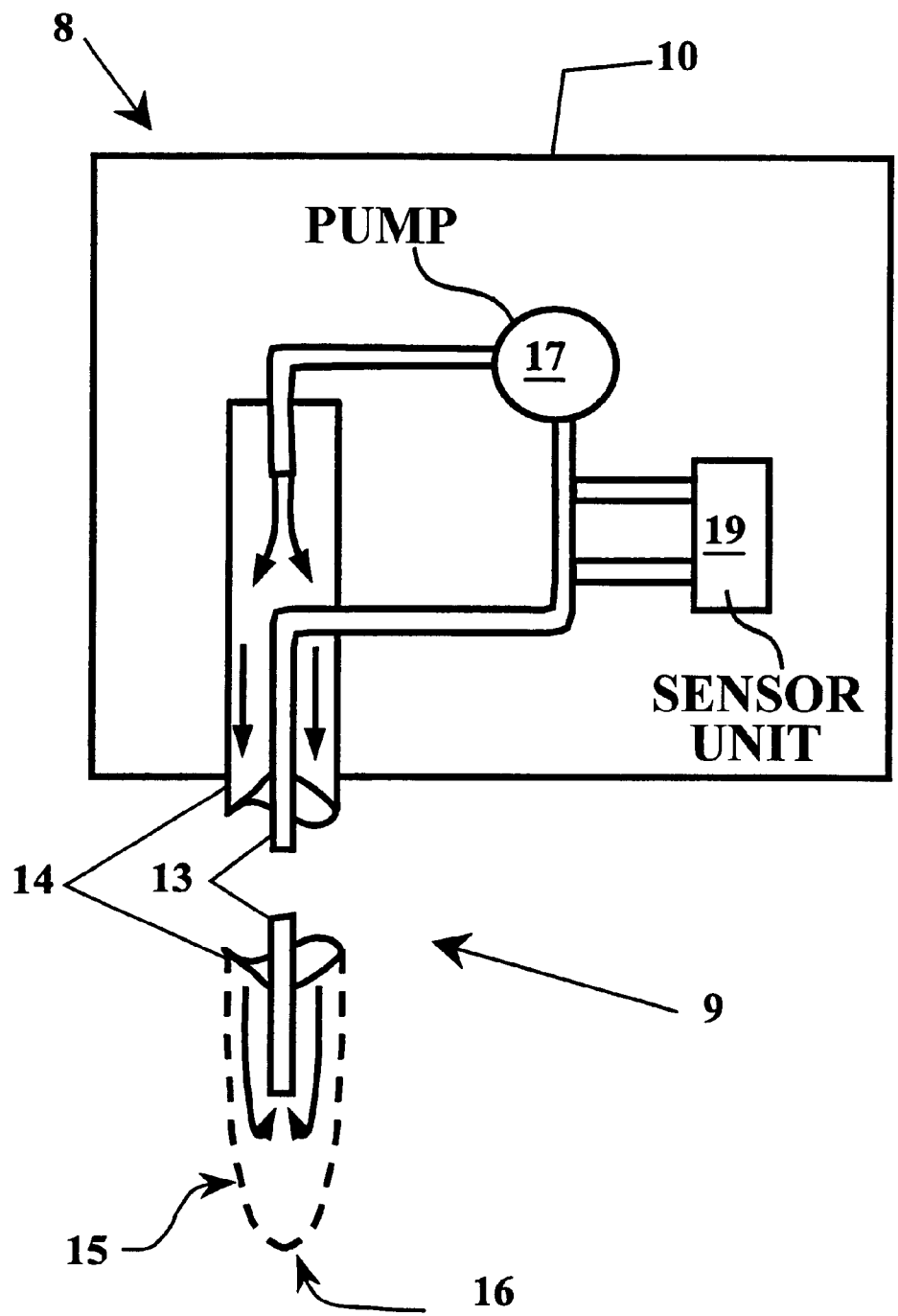
FIG. 2 shows details of an embodiment of the monitor useable in the situation of FIG. 1.

FIG. 2 shows an embodiment of the monitor 8 according to the present invention useable in the intensive care situation depicted in FIG. 1. The catheter probe 9 is shown as having a concentric arrangement of inner and outer lumens 13, 14 respectively. The outer lumen 14 is made of a fluid tight material except for a region 15 which in use is intended to contact the patient's blood and which is made of a permeable material selected to permit the chemicals of interest to migrate through it. The inner lumen 13 is impermeable to these chemicals and ends just short of the catheter tip 16.

Both lumens 13,14 are connected to a housing 10 within which the lumens 13 and 14 are separated. The inner lumen 13 is passed through the wall of the outer lumen 14, to a peristaltic pump 17 and back into the outer lumen 14 which terminates in the housing 10. In this manner a closed flow path (shown by the arrows within the catheter 9) is formed for a probe fluid, such as a saline solution.

Figure 3:
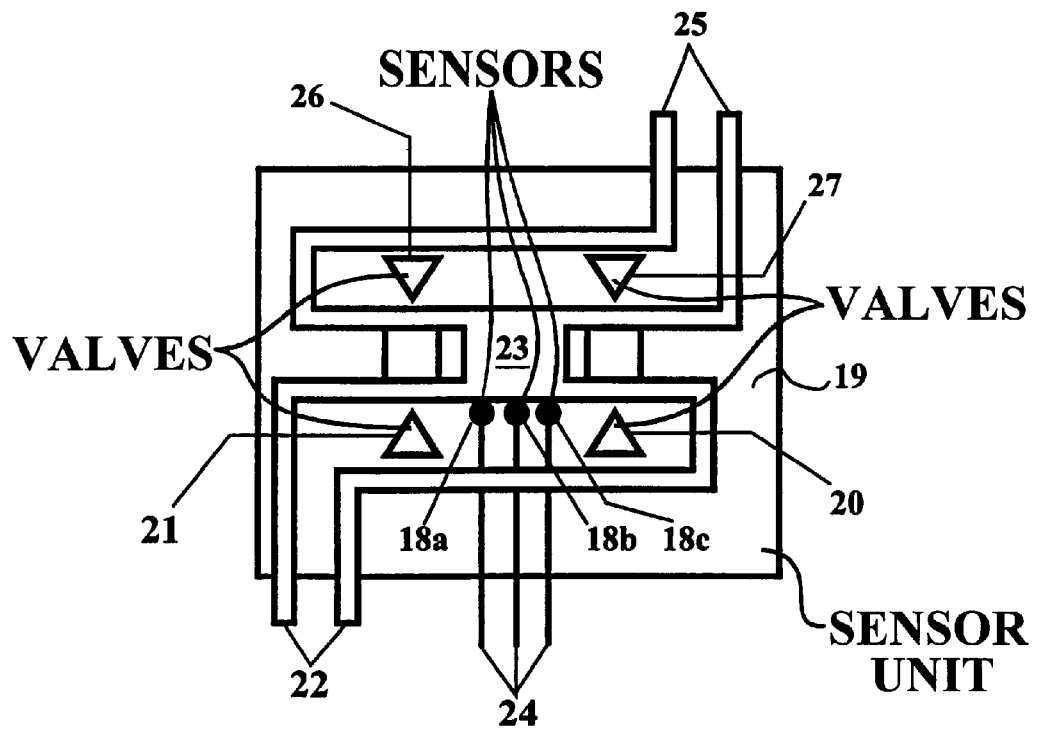
FIG. 3 shows details of a sensor unit useable with the monitor of FIG. 2.

Within the housing 10 the inner lumen 13 is connected a sensor unit 19 in a manner which enables the unit 19 to be isolated from the flowing probe liquid. Referring to FIG. 3, two valves 20 and 21 are disposed on opposite sides of a sample chamber 23 of the sensor unit 19 and synchronously open and close to periodically exchange liquid samples with the inner lumen 13. That is, with both valves 20, 21 open the pump 17 acts to drive liquid from the lumen 13, along the flow path 22, through the valve 20 and into the sample chamber 23. The same amount of liquid is displaced from the sensor unit 19, through the valve 21, to return to the inner lumen 13. When the new sample has replaced the old in the sensor unit 19 the valves 20, 21 are closed and a new analysis is made by sensors 18a . . . c. As the sample volume in this system is much less than the total volume of the probe liquid, the valves 20, 21 are closed for much longer than they are open so that the probe liquid is cycled past the permeable region 15 of the catheter 9 several times before a new sample is taken. Thus a large, substantially the entire, volume of the liquid reaches equilibrium with the blood. It should be noted that a change in the treatment (by means of a ventilator or other equipment) of a patient will normally not have an instantaneous effect on the measured level of diffusable blood chemicals since a systemic exchange between the treatment and the body (such as the gas exchange between gases in the lungs and in the blood system) first must occur before the parameter of interest is affected. This could in some circumstances take up to a couple of minutes, depending on the individual case and the parameter to be measured. It may therefore be sufficient to periodically open the valves 20, 21 at this related rate, which in most, cases will ensure that the entire liquid volume is in equilibrium between sample extractions.

One or more of any known optical, electrochemical or similar sensors 18a . . . c are disposed within the chamber 23 to analyze any fluid within it and can be arranged to communicate with devices external to the monitor 8 using any known telemetric techniques, for example electrically conducting cables 24, or optical or radio frequency transmitter/receiver arrangements (not shown). In the present case, where it desired to analyze blood gasses, suitable sensors may be an oxygen electrode 18a, such as a Clark type electrode, a carbon dioxide electrode 18b, such as commonly available glass electrodes or an Ion Selective Field Effect Transistor (ISFET) and an electrode, such as an ISFET, with a suitable chemically sensitive covering 18c, to selectively sense the presence of electrolytes. These are all well known in the art so that it is not necessary to describe the sensors 18a . . . c in further detail. Furthermore, as such electrodes are well known in the art and may be chosen dependent on the parameters to be measured, the above selection is not intended to be a limitation to the scope of the present invention.

A second flow path 25 is provided within the unit 19 which also provides a fluid communication with the sample chamber 23 via control valves 26, 27 and is used to introduce calibration fluid to the sensors, for example from a source external to the housing 10, typically when valves 20, 21 are closed. This second flow path 25 also may used to introduce a flushing fluid into the chamber 23 when it is desirable not to contaminate the probe liquid with calibration fluid, or may be used to introduce new probe liquid into the monitor 8.

The valves 20, 21, 26, 27 may all be fabricated using standard micromechanical techniques or may be standard magnetic or pressure controlled valves.

Figure 4:
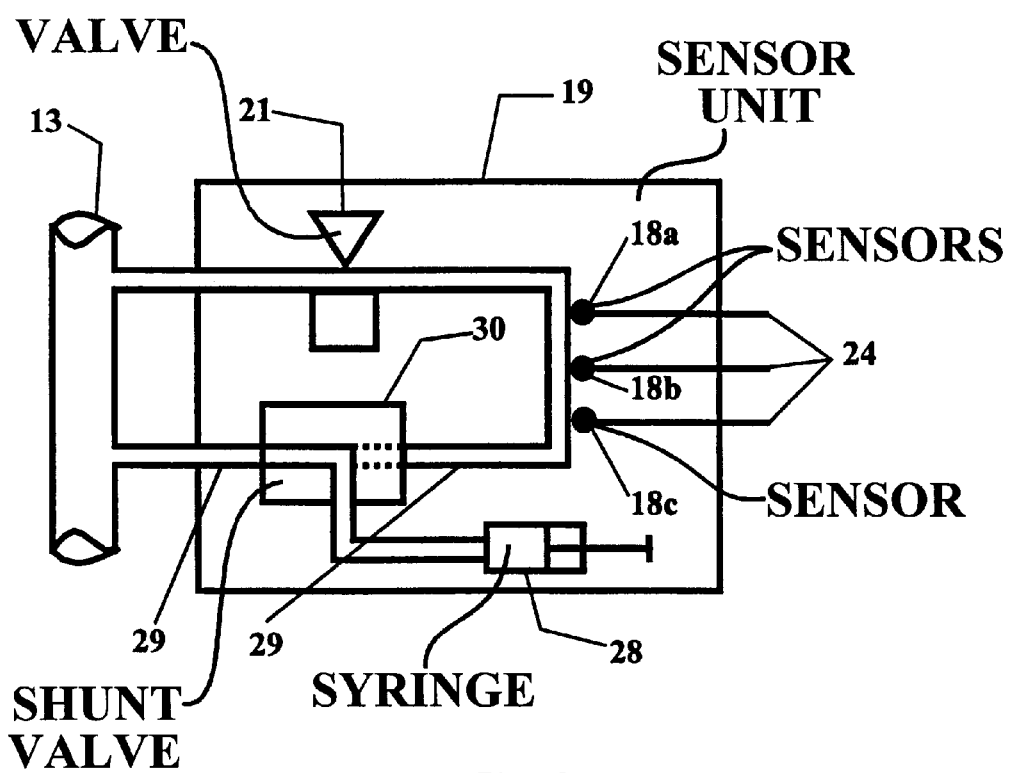
FIG. 4 shows details of an alternative sensor unit of a monitor according to the present invention.

A further embodiment of a sensor unit 19, usable in the monitor according to the present invention, having an alternative extraction instrument 28 is shown in FIG. 4. Components that are common to FIG. 4 and FIGS. 2 and 3 are given the same reference numerals. Here a miniature syringe 28 is used to extract a sample of probe liquid for analysis by the sensors 18a . . . c. The syringe 28 is connected to a fluid conduit 29, which is disposed between the inner lumen 13 and the sensors 18a . . . c, by means of a variable flow path, such as a shunt valve 30. The shunt valve 30 is moveable between a position in which liquid can be drawn into the syringe 28 from the inner lumen 13 and a position in which liquid may be expelled from the syringe 28 to provide a sample at the sensors 18 . . . . c.

Although the embodiments contained herein are described in connection with the monitoring of blood gasses this is not intended to be a limitation on the scope of the invention. It will be understood that the monitor of the above embodiments could be readily adapted to measure other diffusable chemical substances such as glucose or $H^+$ ions; that the double lumen catheter could be replaced with any dialysis type catheter; and that the body fluid need not be inside the body during analysis without falling outside the scope of the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A monitor for analyzing a body fluid for diffusable chemical substances, comprising:
   a probe having a region permeable to chemical substances of interest, and means adapted for placing said region into communication with a body fluid in a subject to be analyzed;
   a sensor in liquid communication with said probe, said sensor emitting an output signal dependent on a presence of said chemical substance of interest;
   a pumping system for transporting a sample of liquid from said region of said probe to said sensor; and a closed fluid flow path including said pumping system and said sensor, said pumping system circulating said sample a plurality of times around said closed fluid flow path and said sensor analyzing said sample only after said sample has circulated in said closed fluid flow path for said plurality of times.

2. A monitor as claimed in claim 1 wherein said pumping system comprises a pump for producing a pulsed liquid circulation in said closed fluid flow path.

3. A monitor as claimed in claim 2 wherein said pump comprises a peristaltic pump.

4. A monitor as claimed in claim 1 wherein said sensor is disposed outside of said closed fluid flow path, and further comprising extraction means, communicating with fluid in said probe, for periodically extracting a sample from said fluid in said probe for supply to said sensor for analysis by said sensor.

5. A monitor as claimed in claim 4 wherein said extraction means comprises a liquid conduit having opposite ends connected to said closed fluid flow path, and valves disposed within said conduit for periodically isolating said liquid conduit from said closed fluid flow path and communicating said liquid conduit with said closed fluid flow path.

6. A monitor as claimed in claim 4 wherein said extraction means comprises a syringe for withdrawing fluid from said probe and for transporting fluid drawn from said probe to said sensor for analysis.

\* \* \* \* \*